US006412345B1

(12) United States Patent
Murray et al.

(10) Patent No.: US 6,412,345 B1
(45) Date of Patent: Jul. 2, 2002

(54) BALANCING OF ROTATIONAL COMPONENTS OF CT IMAGING EQUIPMENT

(75) Inventors: Thomas R. Murray, Delafield; Richard C. Boettner, Milwaukee; Philip M. Wiggin, Delafield, all of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/676,303

(22) Filed: Sep. 29, 2000

(51) Int. Cl.[7] ................................................ G01M 1/16
(52) U.S. Cl. ............................ 73/468; 73/462; 73/466
(58) Field of Search ........................ 73/468, 460, 462, 73/466

(56) References Cited

U.S. PATENT DOCUMENTS

| | | |
|---|---|---|
| 4,272,696 A | 6/1981 | Stroble et al. |
| 4,393,511 A | 7/1983 | Jens |
| 4,569,070 A | 2/1986 | Schubert et al. |
| 5,672,824 A | * 9/1997 | Chiu-Wei .................... 73/468 |
| 5,689,543 A | 11/1997 | Graves et al. |

\* cited by examiner

*Primary Examiner*—Richard A. Moller
(74) *Attorney, Agent, or Firm*—Carl B. Horton, Esq.; Armstrong Teasdale LLP (57) ABSTRACT

One aspect of the present invention is therefore a method for balancing a hollow cylindrical, rotatable object that is coupled to a drive source that is configured to rotate the rotatable object without a central shaft. The method includes steps of: mounting an arbor having a forward shaft and an aft shaft to an inner wall of the rotatable object so that the forward shaft and aft shaft are concentric to an axis of rotation of the rotatable object; operating the drive source to rotate the rotatable object and the arbor; measuring displacement of the forward shaft and the aft shaft of the arbor while the drive source is rotating the rotatable object; applying balancing weights to the rotatable object in accordance with the measured displacements; and removing the arbor from the rotatable object when a balance is achieved.

The above-described method for balancing a rotatable object is suitable for balancing CT imaging systems both at the end of a manufacturing cycle as well as in the field after component replacement. In addition, because the system is integral, it is not necessary to uncouple the rotatable object from the frame of the CT gantry to balance the rotatable object.

18 Claims, 6 Drawing Sheets

BALANCING OF ROTATIONAL COMPONENTS OF CT IMAGING EQUIPMENT

BACKGROUND OF THE INVENTION

This invention relates generally to methods and apparatus for balancing of relatively slowly rotating objects having large open bores with no central shafts, and more particularly to methods and apparatus for balancing of such rotating equipment as is found in computed tomography (CT) imaging systems.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

The rotational speed of gantries of CT scanners has continued to increase, until CT scanners now produce rotational speeds of 120 revolutions per minute (RPM). Speeds are expected to continue to increase. However, as rotational speeds increase, so does the need to dynamically balance the rotating portion of the scanner.

The balancing of rotational equipment is not a new concept. Balancing technology is well-understood, and several companies produce commercial balancing equipment. However, because of the nature of CT imaging system design, there are a number of reasons why traditional balancing equipment will not work with a CT system. Some of the more significant reasons include the following:

Most rotating equipment that is balanced by commercial equipment has a solid central shaft; for example, electric motors and fans. CT equipment, on the other hand, has a large, open bore, typically about 700 mm or larger.

Most rotating equipment has two bearings positioned at opposite ends of the rotating member. By contrast, the main bearing member of a CT imaging system has either one bearing, or two bearings that are positioned very close to each other.

Most commercially available balancing equipment requires rotational speeds of 100 RPM or more to accurate balance a rotating system, as most equipment requiring balancing rotates as 1000 RPM or higher. CT imaging systems not having the highest rotational speed capability do not reach the minimum rotational speed required by the balancing equipment, and systems having the highest rotational speeds barely reach the minimum.

Also, typical rotating equipment usually has its center of gravity (CG) positioned between its two support bearings, and rarely has much of its rotating load cantilevered. By contrast, most CT imaging systems have an over-hung load, relative to the system's main bearing plane.

Figure 3:
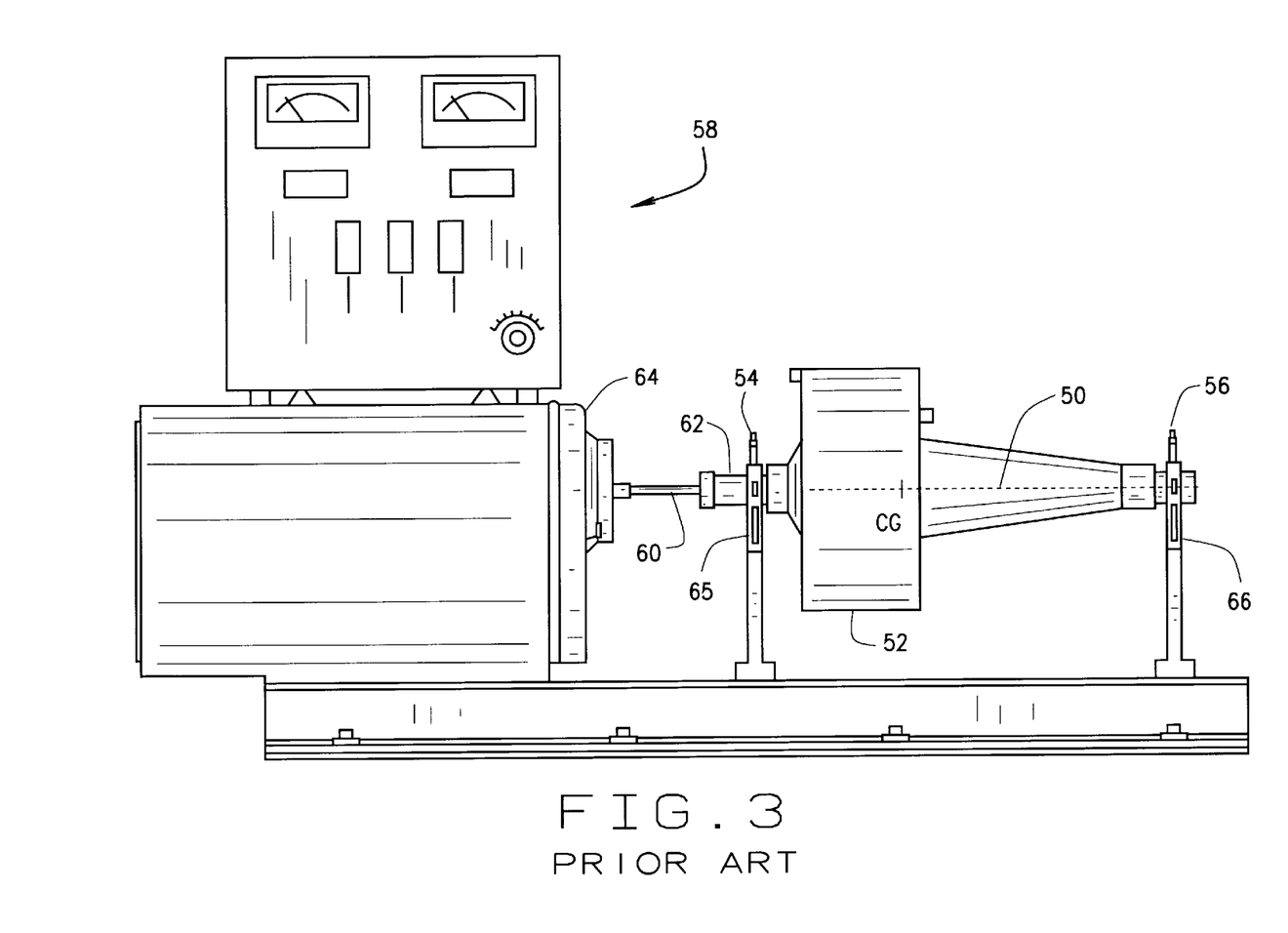
FIG. 3 is a pictorial illustration of a prior art balancing machine, illustrating one method of conventional balancing.

FIG. 3 illustrates one method by which conventional balancing is performed. An axis 50 of a rotating member 52 is positioned horizontally, with the center of gravity CG placed between two elastic mounts 54, 56 of a balancing machine 58. A coupling 60 of balancing machine 58 is rotatably coupled to a shaft 62 of rotating member 52. A drive mechanism 64 of balancing machine 58 rotates coupling 60 which causes rotating member 52 to rotate. A nonsymmetrical distribution of weight around axis 50 of rotating member 52 results in translational motion of both elastic mounts 54, 56. Balancing machine 58 measures translational motion of both elastic mounts 52, 54 via accelerometers 65, 66, as well as the relative phasing of their motion. Adjustments are made (if any are necessary) in the distribution of weight of rotating member 52 to reduce the translational motion, the redistribution being a function of the relative phasing of motion. Once satisfactorily balanced, rotating member 52 goes through a final assembly and is usually never subsequently modified, serviced, or replaced.

With CT imaging systems, there are at least two problems with the above approach. First, the rotating member of a CT imaging system is comprised of several discrete components, some mechanical and some electrical. Throughout the life of the CT imaging system, any one of these components may require modification or replacement, potentially unbalancing the system.

Also, because the rotating mass of a CT imaging system is overhung, there is no "second" mount available to measure the motion and the angular phasing of the imbalance of the rotating mass. The frame of the CT gantry cannot be used as a secondary mount for measuring the motion of the rotating mass due to the confounding of motion information from the natural resonant motion of the frame itself (i.e., the accelerometer senses motion from both the rotating mass and the frame, whereas dynamic balancing requires just the motion of the rotating mass).

It would therefore be desirable to provide methods and apparatus for balancing a CT imaging system both at the end of a manufacturing cycle as well as in the field after component replacement.

BRIEF SUMMARY OF THE INVENTION

One aspect of the present invention is therefore a method for balancing a hollow cylindrical, rotatable object that is coupled to a drive source that is configured to rotate the rotatable object without a central shaft. The method includes steps of: mounting an arbor having a forward shaft and an aft shaft to an inner wall of the rotatable object so that the forward shaft and aft shaft are concentric to an axis of rotation of the rotatable object; operating the drive source to rotate the rotatable object and the arbor; measuring displacement of the forward shaft and the aft shaft of the arbor while the drive source is rotating the rotatable object; applying balancing weights to the rotatable object in accordance with the measured displacements; and removing the arbor from the rotatable object when a balance is achieved.

The above-described method for balancing a rotatable object is suitable for balancing CT imaging systems both at the end of a manufacturing cycle as well as in the field after component replacement. In addition, because the rotatable object is balanced using an integral system, it is not necessary to uncouple the rotatable object from the frame of the CT gantry.

DETAILED DESCRIPTION OF THE INVENTION

Figure 1:
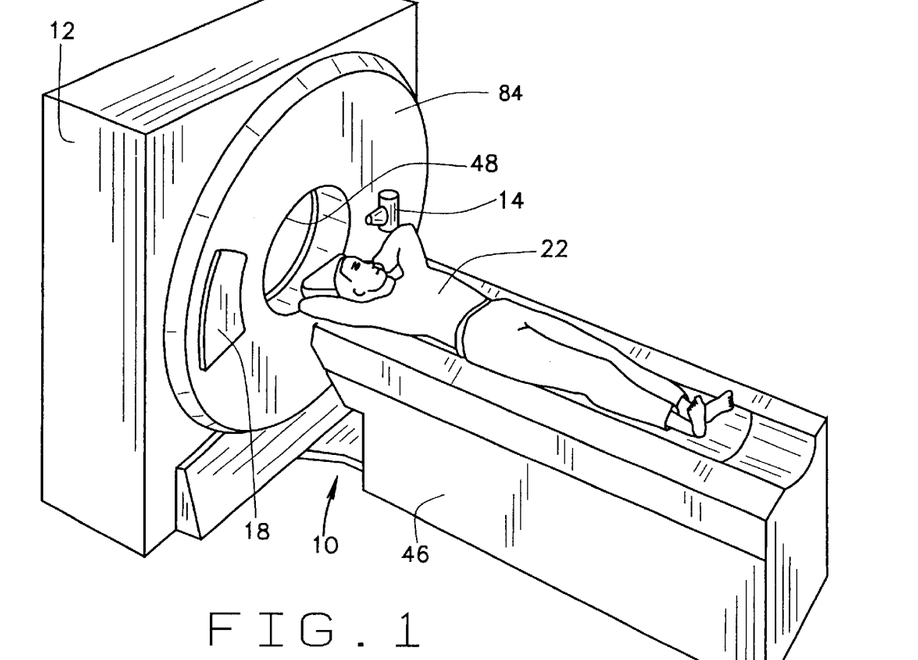
FIG. 1 is a pictorial view of a CT imaging system.
Figure 2:
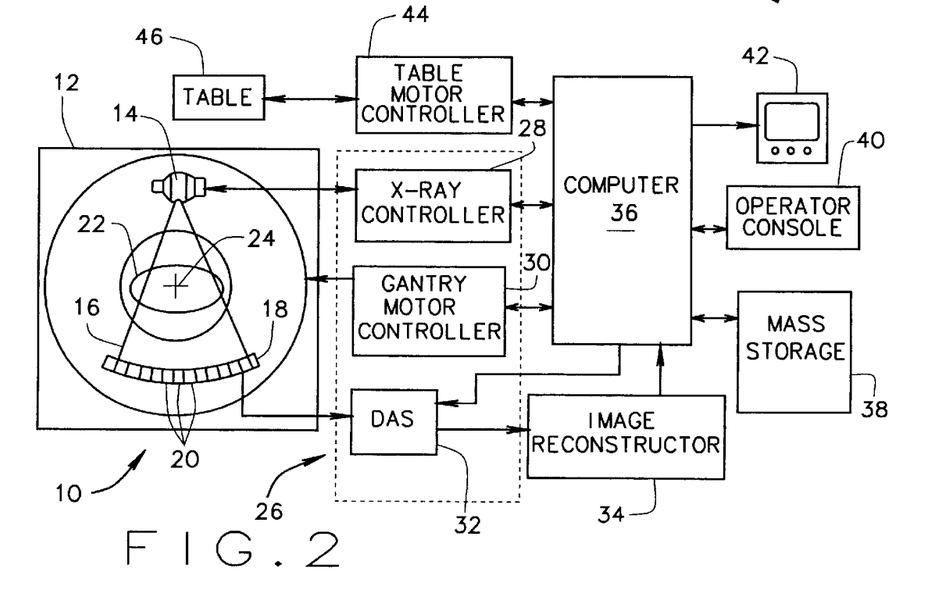
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. Detector array 18 may be fabricated in a single slice or multi slice configuration. In a multi-slice configuration, detector array 18 has a plurality of rows of detector elements 20, only one of which is shown in FIG. 2.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 4:
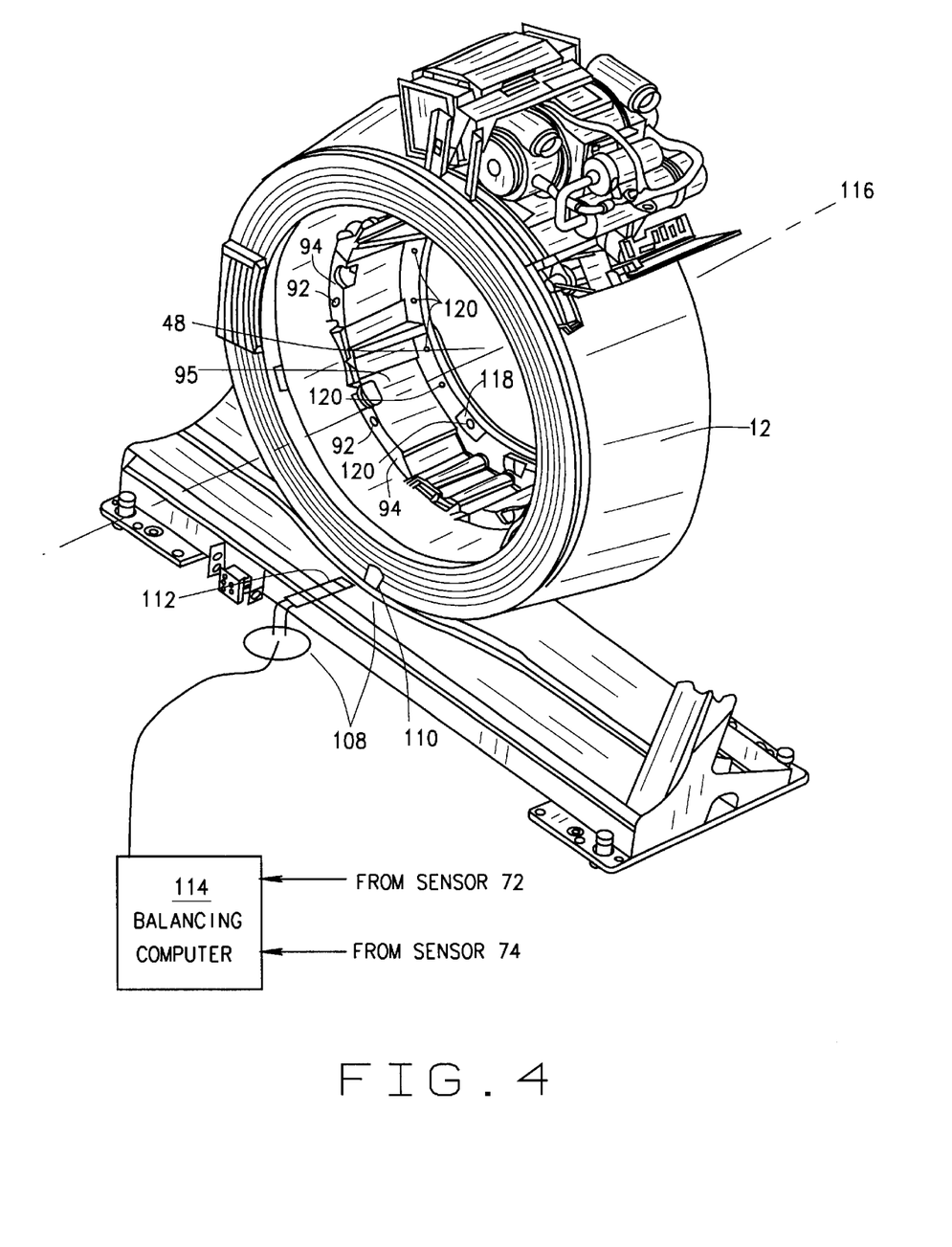
FIG. 4 is a simplified, partial cut-away view of the inside of the CT imaging system of FIG. 1, showing a rotatable object or gantry that is rotated with an axial drive mechanism that rotates the gantry without using a central gantry shaft; an axial position encoder of one embodiment of the present invention is also shown. (Many components of the CT imaging system have been omitted or simplified in this illustration to more clearly illustrate the present invention.)

A partial cut-away perspective view of imaging system 10 is shown in FIG. 4. In this view, many structures of imaging system 10 unnecessary for a full understanding of the present invention have been omitted. Gantry 12 is rotated with an axial drive mechanism (not shown) coupled to imaging system 10 and configured to rotate gantry 12 without use of a central gantry shaft, thus leaving gantry opening 48 free to accept patient 22 as table 46 moves. The axial drive mechanism is known in the art. Rotation of gantry 12 is accomplished, for example, by coupling the axial drive mechanism to a wall of gantry 12, which is essentially cylindrical in shape and has a large central opening or hollow 48.

In one embodiment of the present invention and referring to FIGS. 5, 6, 7, and 8, an arbor 70 is used for measurement of motion and angular phasing of rotating gantry 12 and associated components including radiation source 14 and detector array 18. Motion of the rotating mass 12 and its associated components is measured via a first non-contacting proximity sensor 72 and a second non-contacting proximity sensor 74 in a first plane 76 and a second plane 78, respectively, by introducing a precisely positioned and balanced central shaft of arbor 70, more specifically an aft sensing disk 98 and a forward sensing disk 100 simulate rotor shafts. Arbor 70 itself is precisely balanced using conventional rotating balance techniques independently of gantry 12. Using arbor 70, it is not necessary to obtain balancing measurements directly from gantry 12 or gantry frame 84 (shown in FIG. 1). In one embodiment, sensing disks 98 and 100 are fixed, so that they rotate with the rotating mass of gantry 12 and associated components.

Balancing arbor 70 is a rigid structure built to minimize motion via flexing. In one embodiment, arbor 70 is constructed from a lightweight metal such as aluminum, and is balanced and precisely positioned to minimize motion due to runout. As such, the interjection of misleading motion into balancing algorithms is avoided. In the illustrated embodiment, balancing arbor 70 comprises a ring 86 having a diameter that allows it to fit inside gantry opening 48. Tabs 88 at the circumference of ring 86 are provided with holes 90 for bolting ring 86 onto precisely positioned mating holes 92 in a ridge or flange 94 of an inner wall 95 of gantry 12 (as shown in FIG. 4) using bolts 96. (In the embodiment represented by FIG. 4, ridge or flange 94 is located in a central portion of inner wall 95 of gantry opening 48, but in another embodiment, it is a flange at one end of gantry opening 48.) In one embodiment, ridge or flange 94 is provided with an additional means for locating and/or holding ring 86 into position, such as wells (not shown) in ridge 94 that are configured to position and to retain tabs 88.

Figure 5:
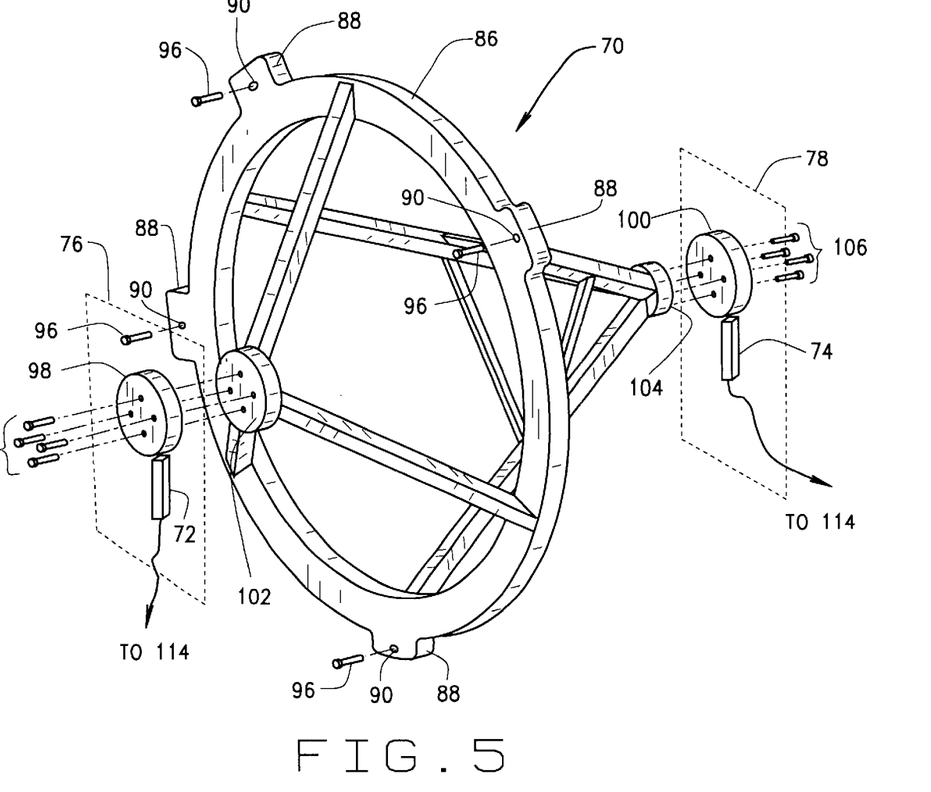
FIG. 5 is a perspective view of an arbor of one embodiment of the present invention.
Figure 6:
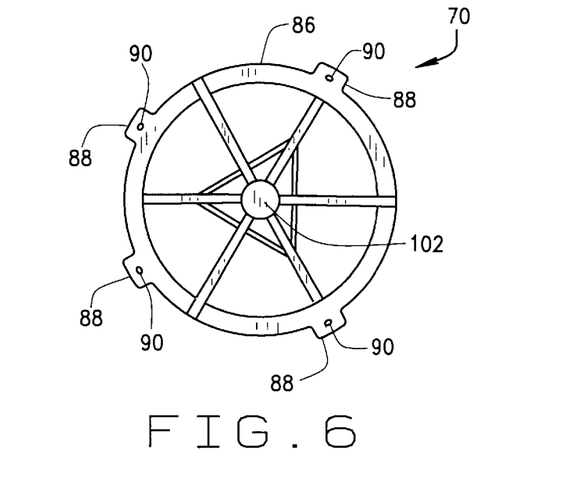
FIG. 6 is a aft view of the arbor of FIG. 5.
Figure 7:
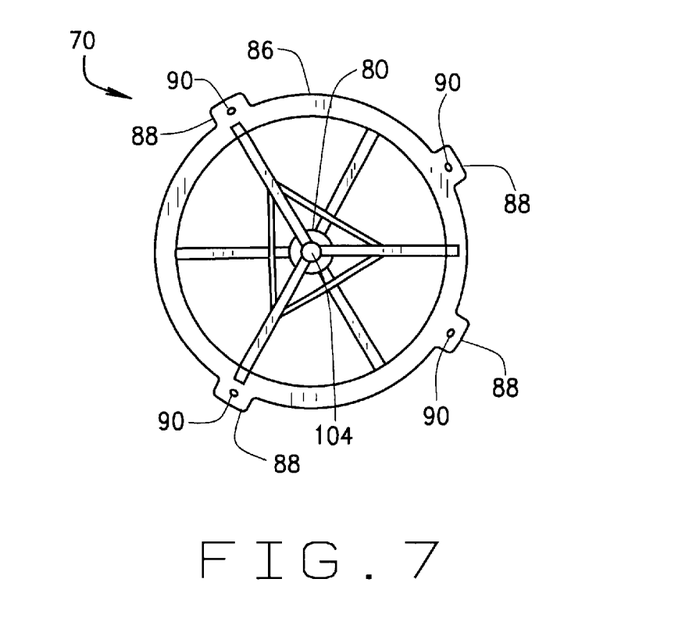
FIG. 7 is an front view of the arbor of FIG. 5.
Figure 8:
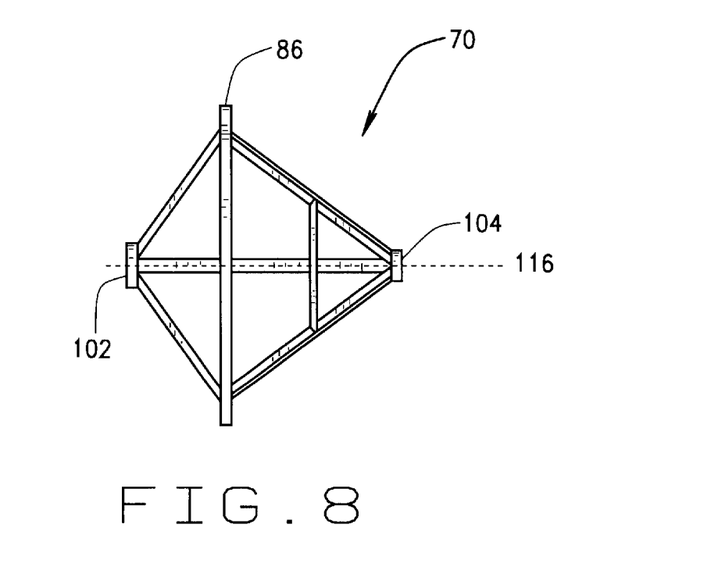
FIG. 8 is a side view of the arbor of FIG. 5.

In one embodiment and referring to FIG. 5, a first sensing disk 98 and a second sensing disk 100 are affixed to first end 102 and second end 104 of arbor 70, respectively, using bolts 106. Sensing disks 98 and 100 are used in conjunction with first noncontacting proximity sensor 72 and second noncontacting proximity sensor 74, respectively, to measure balance of rotating gantry 12. In one embodiment, sensing disks 98 and 100 are made of a material optimized for use with sensors 72 and 74. For example, sensing disks 98 and 100 are stainless steel disks, and sensors 72 and 74 are either capacitive or inductive sensors mounted on isolated stands (not shown). Disks 98 and 100 define first and second planes 76 and 78, respectively.

Figure 9:
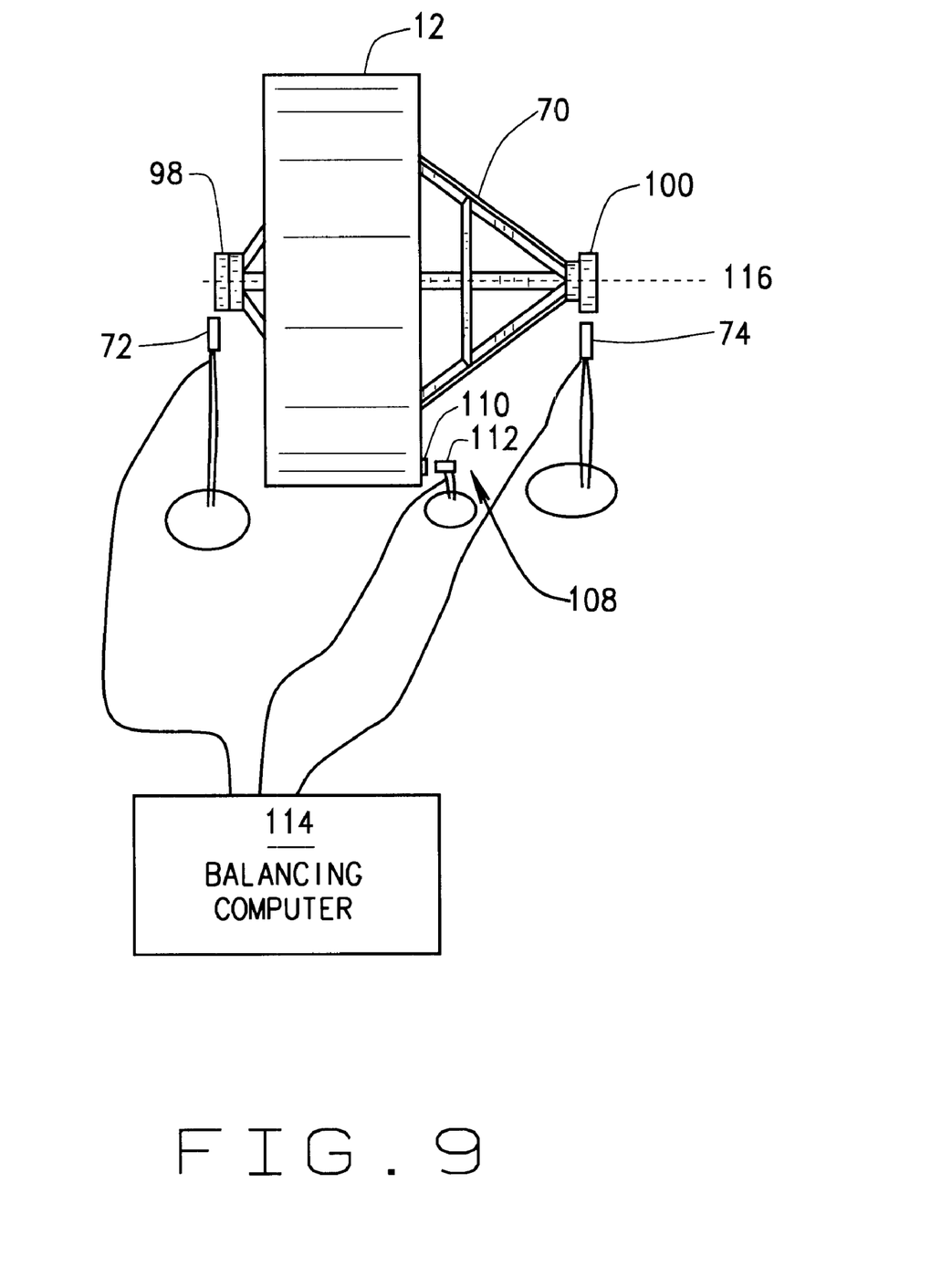
FIG. 9 is a simplified representation of the arbor of FIG. 5 mounted in the cylindrical gantry of FIG. 4, and of the locations of noncontact proximity sensors for sensing motion of the shafts of the arbor in one embodiment of the present invention. Also used in this embodiment are an axial position encoder and a balance computer, which are also represented in FIG. 9 in simplified block diagram form.

In one embodiment of the present invention, and referring to FIGS. 4, 5, and 9, an axial drive mechanism is used to rotate gantry 12 for balancing. An axial position encoder 108 is used for angular sensing of phasing. In one embodiment in which gantry 12 is rotated at a constant rate, axial position encoder 108 is simply a piece of reflective tape 110 mounted on gantry 12 used in conjunction with an infrared (IR) or other optical sensor 112. Optical sensor 112 senses reflected IR or other light from reflective tape 110 as gantry 12 rotates, thereby defining times at which gantry 12 has rotated a multiple of 360° from an angular reference position. Other types of axial position encoders 108 are also suitable for use with the present invention. Non-contacting proximity sensors 72, 74 external to gantry 12 are used to detect rotating mass displacement. Sensors 72 and 74 detect displacement of the rim of sensing disks 98 and 100, respectively, which represents an out-of-balance condition. Sensing information or data from sensors 72, 74, and axial position encoder 108 are fed to a balancing computer 114. Balancing computer 114 computes both static and dynamic coupled imbalance from the displacements indicated by sensors 72 and 74, and the phase of these displacements relative to each other and to the position of gantry 12 indicated by axial position encoder 108. Sensing disks 98 and 100 of arbor 70 are configured so that, when arbor 70 is mounted on gantry 12, disks 98 and 100 are concentric to rotational axis 116 of CT imaging system 10. Sensing disks 98 and 100 are used to transmit the motion of the rotating mass of gantry 12 and associated components to proximity sensors 72, 74, but do not, and are not required to support the rotating mass of gantry 12 and associated components. Zero, one, or more balancing weights 118 are placed at appropriate locations on gantry 12 based on the informational output of balancing computer 114. In one embodiment, weights 118 are bolted to gantry 12 at an appropriate selection of one or more strategically placed, pre-drilled gantry 12 locations 120. Other methods for attaching balancing weights 118 to gantry 12 are used in other embodiments. Arbor 70 is removed from gantry 12 when a satisfactory balance i s achieved.

Sensing planes 76 and 78 are parallel to one another. It has been empirically determined that sensors 72 and 74 provide adequate balancing information when they are configured to detect motions of sensing disks 98 and 100 in the same direction. For example, in one embodiment, rotational axis 116 is parallel to the floor, sensor 72 is configured to sense up and down motion of sensing disk 98 in plane 76. Sensor 74 is similarly configured to sense up and down motion of sensing disk 100 in plane 78. Alternatively, sensors 72 and 74 are configured at any orientation to sense motion around rotational axis 116.

It will b e recognized that embodiments of the present invention do not require an external or additional drive, and no accelerometers are required as are used in conventional balancing equipment. Furthermore, balancing occurs at the rotational rate of imaging system 10 itself, which is at or below the minimum rotational speed of other types of balancing equipment. In addition, the construction details of arbor 70 are not critical. Other arbor 70 constructions having shafts 80 and 82 configured to rotate concentrically with rotational axis 116 of gantry 12 are also suitable. For example, in one embodiment of arbor 70, a circular plate is used in place of ring 86, and forward sensing disk 98 and aft sensing disk 100 are axial cylindrical shafts. In another embodiment, tabs 88 are replaced with other mounting means. For example, in one embodiment, a suitably sized ring 86 (or an equivalent circular plate) has holes 90 near its circumference for mounting bolts 96.

While the invention has been described in terms of various specific embodiments, those skilled in the art will recognize that the invention can be practiced with modification within the spirit and scope of the claims.

What is claimed is:

1. A method for balancing a hollow cylindrical, rotatable object that is coupled to a drive source that is configured to rotate the rotatable object without a central shaft; said method comprising the steps of:

mounting an arbor having a forward shaft and an aft shaft to an inner wall of the rotatable object so that the forward shaft and aft shaft are concentric to an axis of rotation of the rotatable object;

operating the drive source to rotate the rotatable object and the arbor;

measuring displacement of the forward shaft and the aft shaft of the arbor while the drive source is rotating the rotatable object;

applying balancing weights to the rotatable object in accordance with the measured displacements; and balancing the rotatable object using an integral system while the object is coupled to the drive source.

2. A method in accordance with claim 1 wherein measuring displacement of the forward shaft and the aft shaft comprises the step of utilizing noncontact sensors to measure displacement of the forward shaft and the aft shaft.

3. A method in accordance with claim 2 further comprising the steps of:

measuring an angle of displacement of the rotatable object utilizing an axial position encoder; and removing the arbor from the rotatable object when a balance is achieved.

4. A method in accordance with claim 3 wherein measuring an angle of displacement of the rotatable object utilizing an axial position encoder comprises the steps of placing a reflective tape on the rotatable object and sensing a reflection from the rotating place.

5. A method in accordance with claim 1 wherein the rotatable object is a gantry of a computed tomographic (CT) imaging system.

6. A method in accordance with claim 5 wherein measuring displacement of the forward shaft and the aft shaft comprises the step of utilizing noncontact sensors to measure displacement of the forward shaft and the aft shaft.

7. A method in accordance with claim 6 further comprising the step of measuring an angle of displacement of the rotatable object utilizing an axial position encoder.

8. A method in accordance with claim 7 wherein measuring an angle of displacement of the rotatable object utilizing an axial position encoder comprises the steps of placing a reflective tape on the rotatable object and sensing a reflection from the rotating place.

9. A method in accordance with claim 6 wherein the noncontact sensors are capacitive sensors.

10. A method in accordance with claim 6 wherein the noncontact sensors are inductive sensors.

11. A method in accordance with claim 5 wherein operating the drive source to rotate the rotatable object and the arbor comprises operating the drive source to rotate the gantry at a maximum rated operating speed of the drive source.

12. A method in accordance with claim 5 wherein applying balancing weights to the rotatable object in accordance with the measured displacements comprises bolting one or more weights to the gantry at one or more selected, pre-drilled locations.

13. A balancing kit for balancing a hollow cylindrical, rotatable object that is coupled to a drive source that is configured to rotate the rotatable object without a central shaft; said balancing kit comprising:

an arbor having a forward shaft and an aft shaft and configured to be removably mountable to an inner wall of the rotatable object so that the forward shaft and aft shaft are concentric to an axis of rotation of the rotatable object;

at least a pair of noncontact motion sensors, one configured to sense motion of the forward shaft and the other to sense motions of the aft shaft when placed in proximity thereof and the rotatable object is rotated;

a shaft encoder having a portion configured for attachment to the rotatable object, said shaft encoder being configurable to detect a relative angle of rotation of the rotatable object; and a balancing computer configured to receive signals from said noncontact motion sensors and said shaft encoder and to compute a balance of the rotatable object therefrom while the object is coupled to the drive shaft.

14. A balancing kit in accordance with claim 13, wherein said noncontact motion sensors are capacitive sensors.

15. A balancing kit in accordance with claim 13, wherein said noncontact motion sensors are inductive sensors.

16. A balancing kit in accordance with claim 13 wherein said shaft encoder comprises a reflective tape configured for attachment to the rotatable object and a sensor configured to detect reflections from said reflective tape.

17. A balancing kit in accordance with claim 13 wherein said arbor is configured to be removably attached to an inside wall of a rotatable gantry of a computed tomography (CT) imaging system.

18. A balancing kit in accordance with claim 17 wherein said arbor comprises a tabbed ring configured to mount to an inside wall of a rotatable gantry of a computed tomography (CT) imaging system, and a pair of sensing disks, one of said sensing disks mounted at an end of said forward shaft of said arbor, and the other of said sensing disks mounted at an end of said aft shaft of said arbor.

* * * * *